(12) United States Patent
Kuschmierz et al.

(10) Patent No.: US 12,213,644 B2
(45) Date of Patent: Feb. 4, 2025

(54) OPTICAL SYSTEM AND IMAGING METHOD

(71) Applicant: Technische Universitat Dresden, Dresden (DE)

(72) Inventors: Robert Kuschmierz, Dresden (DE); Jurgen Czarske, Dresden (DE); Elias Scharf, Dresden (DE)

(73) Assignee: Technische Universitat Dresden (DE)

( * ) Notice: Subject to any disclaimer, the term of this patent is extended or adjusted under 35 U.S.C. 154(b) by 541 days.

(21) Appl. No.: 17/649,843

(22) Filed: Feb. 3, 2022

(65) Prior Publication Data

US 2022/0248938 A1     Aug. 11, 2022

(51) Int. Cl.
  *G02B 5/02*   (2006.01)
  *A61B 1/00*   (2006.01)
  *G01S 7/497*  (2006.01)

(52) U.S. Cl.
  CPC ...... *A61B 1/00057* (2013.01); *A61B 1/00167* (2013.01); *G01S 7/497* (2013.01); *G02B 5/0205* (2013.01)

(58) Field of Classification Search
  CPC ...... G02B 5/0278; G02B 5/0284; G02B 6/06; A61B 1/00167; A61B 1/07
  See application file for complete search history.

(56) References Cited

FOREIGN PATENT DOCUMENTS

EP    3518017 A1    7/2019
JP    2016202360 A  12/2016

*Primary Examiner* — Ryan D Howard
(74) *Attorney, Agent, or Firm* — BARNES & THORNBURG LLP; Jeffrey R. Stone

(57) ABSTRACT

An optical system and an imaging method are disclosed, wherein the optical system comprises a multifilament conductor and an optical diffuser for imaging an intensity pattern onto the multifilament conductor, the intensity pattern representing phase information of light emitted from one or more three-dimensional objects; wherein the multifilament conductor is configured to transmit the intensity pattern in the form of a plurality of pixels to an evaluation system, and wherein the evaluation system is configured to generate an image based on the intensity pattern transmitted by the multifilament conductor, the image representing the one or more three-dimensional objects.

18 Claims, 16 Drawing Sheets

FIG. 2A
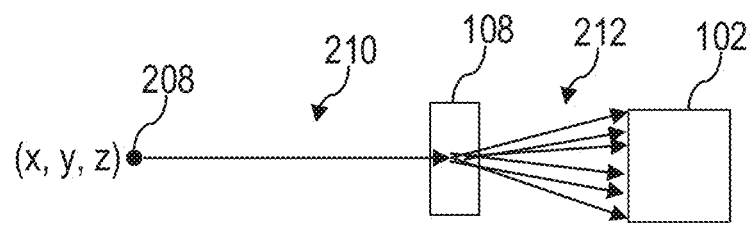
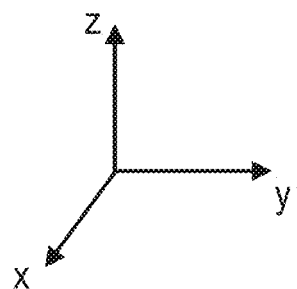
FIG. 2B
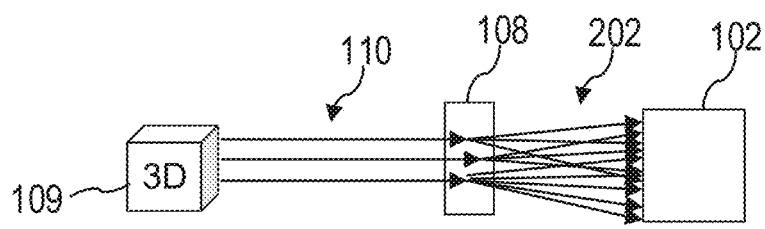
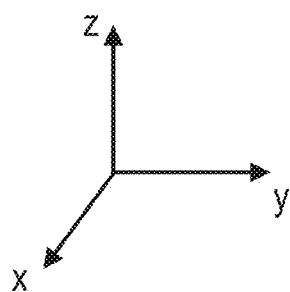

FIG. 4A
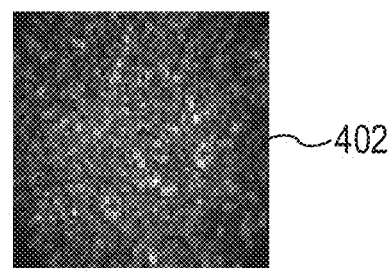
402
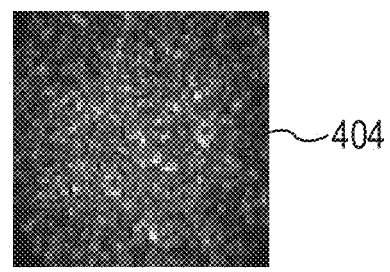
404
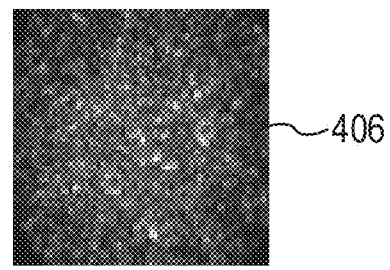
406
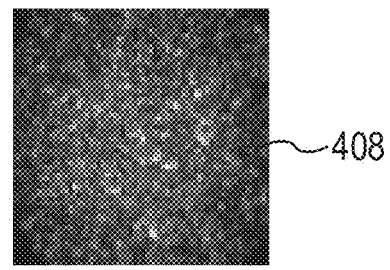
408
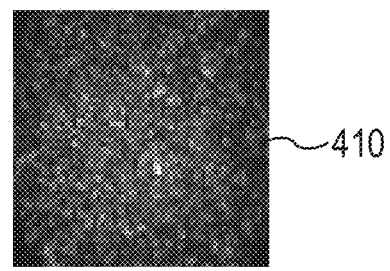
410

FIG. 4B
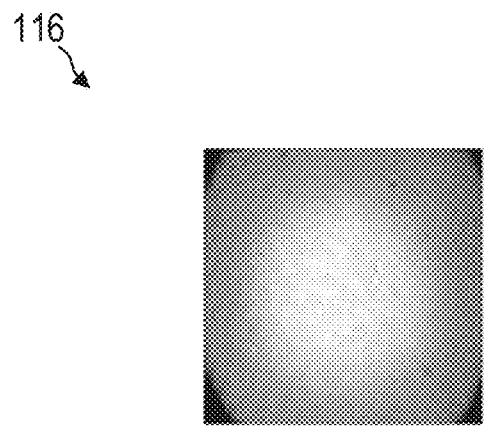
FIG. 4C
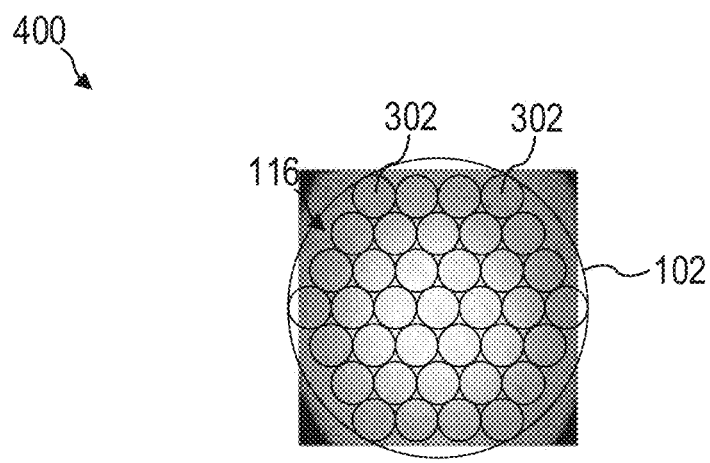
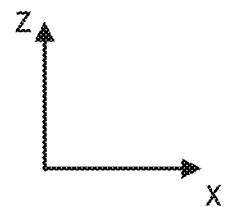

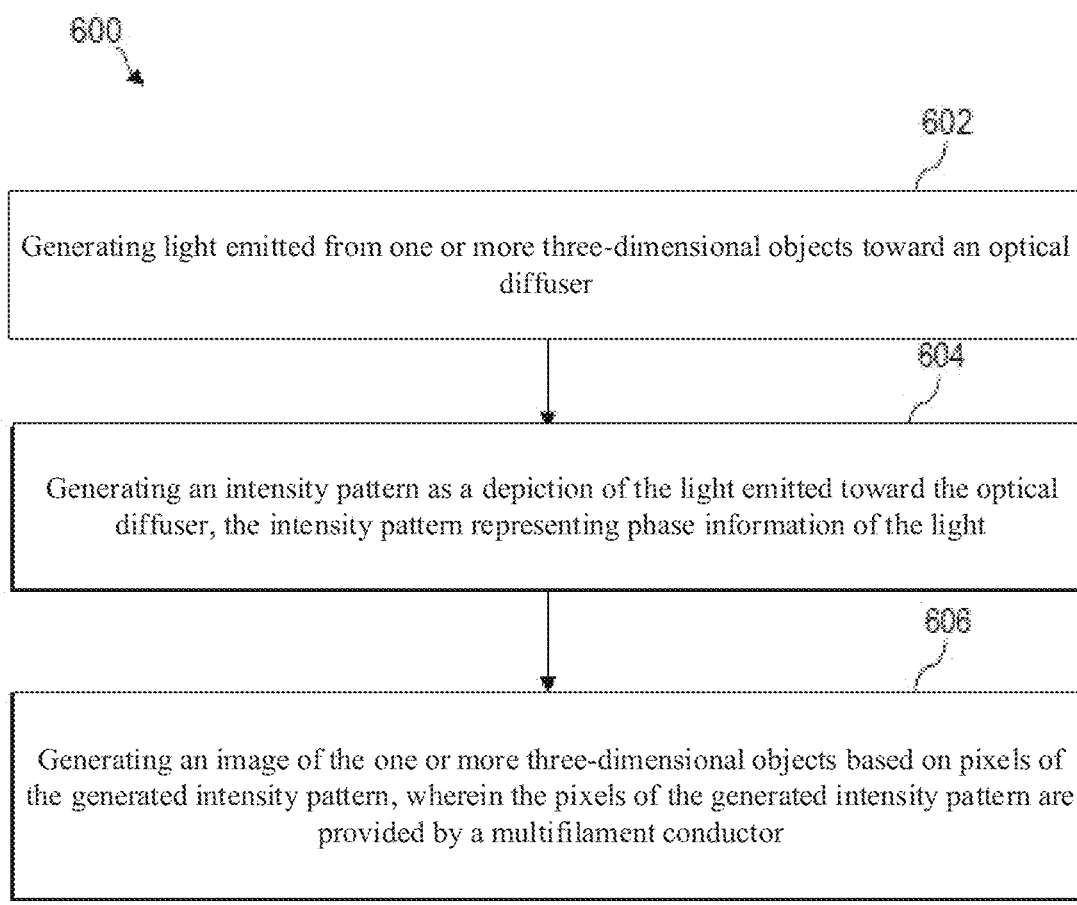

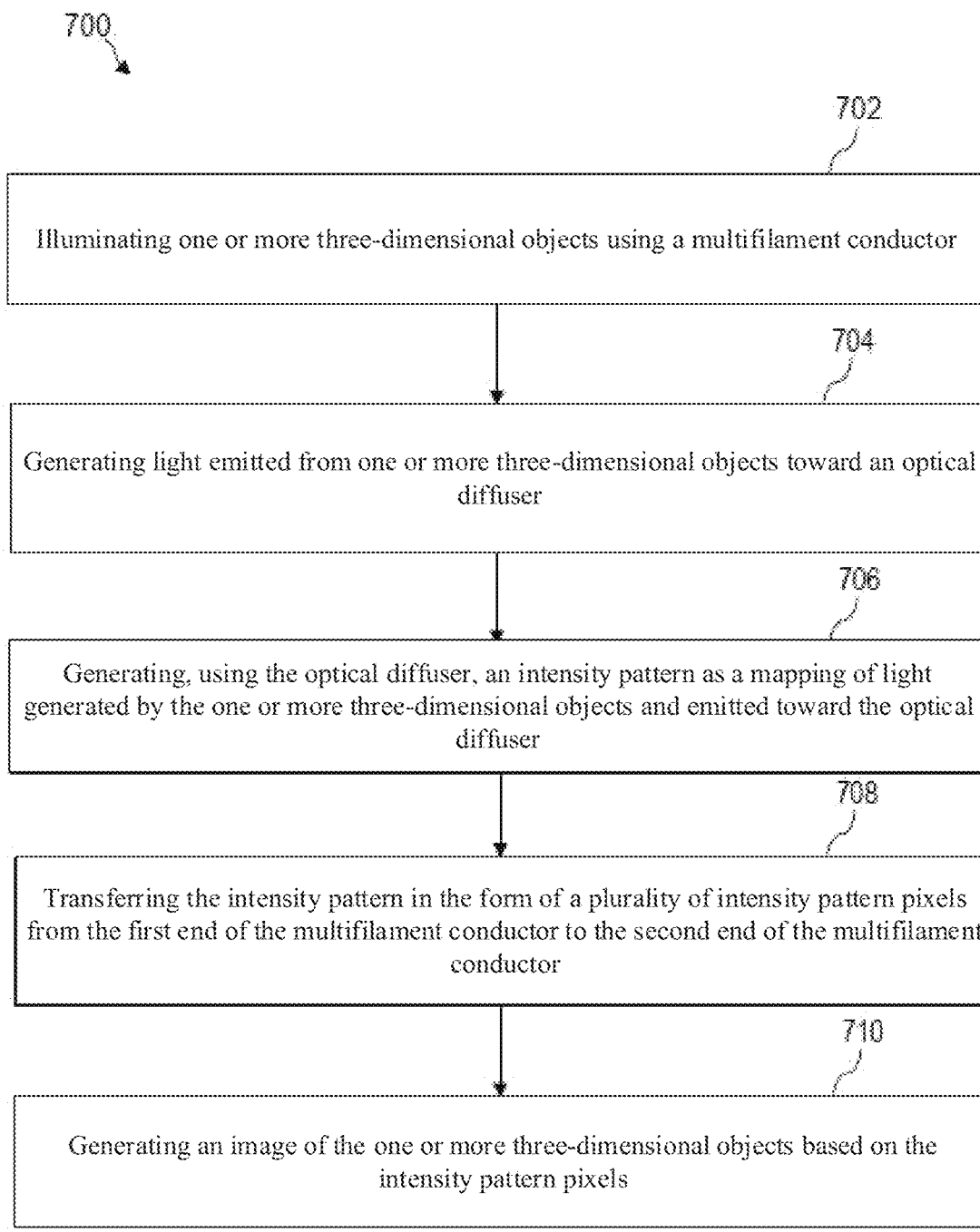

FIG. 10
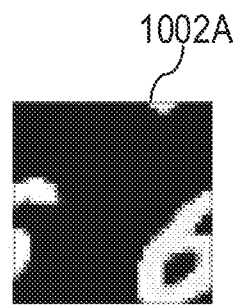
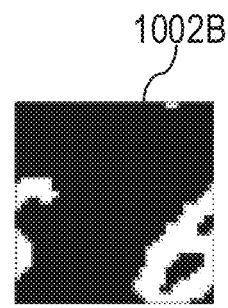
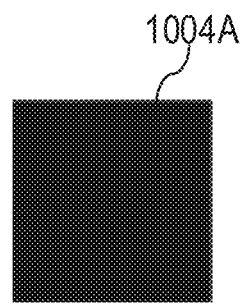
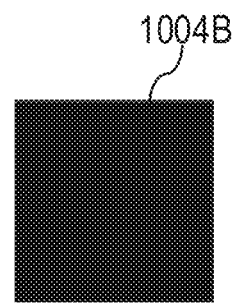
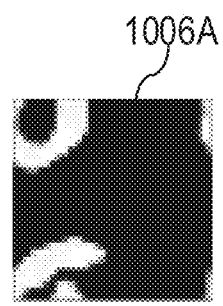
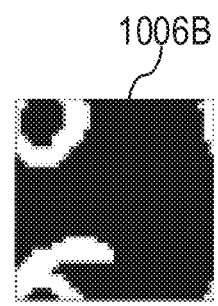

OPTICAL SYSTEM AND IMAGING METHOD

CROSS-CITING TO RELATED APPLICATIONS

This patent application claims priority to German patent application 10 2021 102 755.1, which was filed on Feb. 5, 2021, the entire contents of which are incorporated herein by reference.

TECHNICAL FIELD

Various aspects relate to an optical system and an imaging method.

BACKGROUND

Various optical systems can be used for imaging. For example, endoscopes or endoscopy systems can be used to enable imaging in an opening, such as a body orifice. In this regard, it may be necessary or desirable to depict three-dimensional (3D) objects. For example, 3D video endoscopes with cameras on a probe head that is inserted into an opening may enable three-dimensional imaging. However, electromagnetic compatibility considerations may require that no electromagnetic radiation be emitted from the portion of the endoscope inserted into the opening. Furthermore, when examining a small opening, such as, for example, during endoscopy of a brain, it may be necessary that a maximum diameter or width of the portion of the endoscope inserted into the opening be less than 1 mm. Various holographic endoscopes can achieve both the desired electromagnetic compatibility and a maximum diameter of less than 1 mm by using adaptive optical elements to create a focus that can be controlled in three dimensions. However, this requires a very complex optical setup and therefore has a high cost, both in terms of acquisition and of maintenance. It may be necessary to provide three-dimensional imaging at a reduced cost.

BRIEF DESCRIPTION OF THE DRAWINGS

In the following detailed description, reference is made to the accompanying drawings which form a part thereof and in which are shown, by way of illustration, specific aspects in which the invention may be practiced.

FIGS. 2A to 2D, respectively, an optical diffuser and a multifilament conductor of the optical system according to various aspects;

FIG. 4A exemplary intensity patterns associated with a respective light point source according to various aspects;

FIG. 4B an exemplary intensity pattern according to various aspects;

FIG. 4C an exemplary illustration of an intensity pattern on a multifilament conductor, according to various aspects;

FIG. 6 a method of an imaging process according to various aspects;

FIG. 7 a method of an imaging process according to various aspects;

FIG. 10 exemplary depth images and respective associated training depth images according to various aspects.

DETAILED DESCRIPTION

Figure 1A:
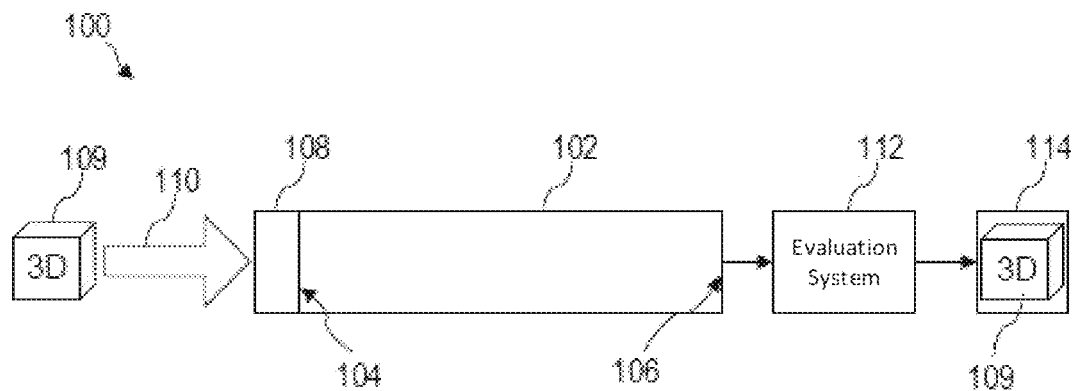
FIGS. 1A to 1D an optical system according to various aspects.

According to various aspects, an optical system and an imaging method are provided that enable three-dimensional imaging at a low cost. Furthermore, the optical system and the imaging method can be realized with a comparatively simple optical setup. This optical assembly may include a portion having a maximum diameter or width of less than 1 mm that may be inserted into an opening. Furthermore, this part can ensure electromagnetic compatibility. The condition that a maximum diameter or width of the part to be inserted into the opening is smaller than 1 mm may result, for example, from the fact that the opening and/or the area to be examined requires a diameter or width smaller than 1 mm. This may be the case, for example, when examining the brain, wherein a diameter and/or width smaller than 1 mm may be required such that a likelihood of damage to the brain is reduced (e.g., minimized). For example, in human endoscopy, a maximum diameter or width of the portion of the endoscope to be inserted may be predetermined (e.g., determined by law).

According to various aspects, an optical system comprises a multifilament conductor and an optical diffuser for imaging an intensity pattern onto the multifilament conductor, wherein the intensity pattern represents phase information of light emitted from one or more three-dimensional objects, wherein the multifilament conductor is configured to transmit the intensity pattern in the form of a plurality of pixels to an evaluation system, and wherein the evaluation system is configured to generate an image based on the intensity pattern transmitted by the multifilament conductor, the image depicting the one or more three-dimensional objects.

An optical system having the features of independent claim 1 forms a first example.

For example, the optical system may be an endoscope, such as a flexible endoscope, or an endoscope system.

The multifilament conductor, in conjunction with the optical diffuser, enables, for example, the transmission of 3D object information. Here, the 3D object information can be transmitted without the need for additional measurement or detection systems, such as a camera, at the end of the multifilament conductor facing the optical diffuser. Furthermore, the 3D object information can be acquired and subsequently analyzed using a comparatively simple optical setup. Furthermore, both the optical diffuser and the multifilament conductor can be implemented with a maximum diameter or width of less than 1 mm.

The optical system may include the optical diffuser being configured to diffuse in transmission and/or in reflection. The features described in this paragraph in combination with the first example form a second example.

The optical system may include the multifilament conductor comprising a first diameter or width at a first end facing the optical diffuser, and the optical diffuser comprising a second diameter or width substantially equal to the first diameter or width. The features described in this paragraph in combination with the first example or the second example form a third example.

The optical system may include the intensity pattern being a speckle pattern. The features described in this paragraph in combination with one or more of the first example to the third example form a fourth example.

The optical system may include each optical waveguide of the plurality of waveguides being configured to transmit an image pixel of the plurality of image pixels from a first end of the multifilament conductor facing the optical diffuser to a second end of the multifilament conductor. The features described in this paragraph in combination with one or more of the first example to the fourth example form a fifth example.

The optical system may include the multifilament conductor being configured to only partially illuminate the one or more three-dimensional objects using one or more optical fibers of the multifilament conductor. The features described in this paragraph in combination with one or more of the first example to the fifth example form a sixth example.

The optical system may include the multifilament conductor being configured to illuminate the one or more three-dimensional objects using light provided to the multifilament conductor by an illumination device. The features described in this paragraph in combination with one or more of the first example through the sixth example form a seventh example.

The optical system may include one or more optical fibers of the plurality of optical fibers being configured to transmit light provided at the second end of the multifilament conductor by an illumination device to the first end of the multifilament conductor for at least partially illuminating the one or more three-dimensional objects. The features described in this paragraph in combination with the fifth example form an eighth example.

The optical system may include the multifilament conductor comprising one or more illumination waveguides configured to transmit light provided at a second end of the multifilament conductor by an illumination device to a first end facing the optical diffuser for at least partially illuminating the one or more three-dimensional objects. The features described in this paragraph in combination with one or more of the first example through the sixth example form a ninth example.

The optical system may include the light provided to the multifilament conductor via the illumination device comprising polychromatic light. The features described in this paragraph in combination with one or more of the seventh example through the ninth example form a tenth example.

The optical system may further include the illumination device being configured to provide light to the multifilament conductor. The features described in this paragraph in combination with one or more of the seventh example through the tenth example form an eleventh example.

The optical system may include that the illumination device being configured to provide polychromatic light to the multifilament conductor, and that the evaluation system is configured to detect a plurality of light colors of the intensity pattern transmitted by the multifilament conductor and to generate the image based on the detected plurality of light colors of the intensity pattern. The features described in this paragraph in combination with the eleventh example form a twelfth example.

The optical system may include the illumination device being configured to provide visible light of a plurality of mutually different light colors to the multifilament conductor in temporal succession; that the multifilament conductor is configured to transmit, for each light color of the plurality of mutually different light colors, a respective intensity pattern representing phase information of light emitted from the one or more three-dimensional objects in the form of a plurality of pixels to the evaluation system; and that the evaluation system is configured to generate the image based on the intensity patterns transmitted by the multifilament conductor for the plurality of mutually different light colors. The features described in this paragraph in combination with the eleventh example form a thirteenth example.

The optical system may include the illumination device being configured to selectively provide light to one or more optical fibers of the multifilament conductor. The features described in this paragraph in combination with one or more of the eleventh example through the thirteenth example form a fourteenth example.

The optical system may include a portion of the multifilament conductor being configured for insertion into an opening, wherein the portion of the multifilament conductor and the optical diffuser have a diameter and/or width of less than 1 mm. The features described in this paragraph in combination with one or more of the first example through the fourteenth example form a fifteenth example.

The optical system may include the evaluation system being configured to generate the image based on the intensity pattern transmitted via the multifilament conductor using a trained neural network. The features described in this paragraph in combination with one or more of the first example through the fifteenth example form a sixteenth example.

The optical system may further include an evaluation system for generating the image. The features described in this paragraph in combination with one or more of the first example through the sixteenth example form a seventeenth example.

The optical system may include the evaluation system being configured to detect a plurality of light colors of the transmitted intensity pattern and to generate the image using the detected plurality of light colors of the intensity pattern. The features described in this paragraph in combination with the seventeenth example form an eighteenth example.

The optical system may include the evaluation system comprising at least one camera for capturing the intensity pattern transmitted via the multifilament conductor, and the evaluation system being configured to generate the image using the captured intensity pattern. The features described in this paragraph in combination with the seventeenth example or the eighteenth example form a nineteenth example. The evaluation system may include a plurality of cameras. According to various aspects, each camera of the plurality of cameras may be configured to detect light of a respective associated wavelength. For example, a first camera may be configured to detect light of a first wavelength, and a second camera may be configured to detect light of a second wavelength different from the first wavelength. According to various aspects, each camera of the plurality of cameras may be configured to detect light of a respective associated polarization state. For example, a first camera may be configured to detect light of a first polarization state, and a second camera may be configured to detect light of a second polarization state different from the first polarization state. According to various aspects, the evaluation system may include multiple cameras for capturing multiple wavelengths (e.g., wavelength ranges) of light and/or multiple cameras for resolving different polarization states of the light.

The optical system may include the evaluation system comprising one or more processors configured to generate the image using the detected intensity pattern. The features described in this paragraph in combination with the nineteenth example form a twentieth example.

The optical system may include the optical system being an endoscope or an endoscope system. The features described in this paragraph in combination with one or more of the first example through the twentieth example form a twenty-first example.

A method (e.g., an imaging method) may comprise: generating light emitted from one or more three-dimensional objects toward an optical diffuser; generating an intensity pattern, via the optical diffuser, as an image of the light emitted toward the optical diffuser, the intensity pattern representing phase information of the light; and generating an image of the one or more three-dimensional objects based on pixels of the generated intensity pattern, wherein the pixels of the generated intensity pattern are provided via a multifilament conductor. The method having the features described in this paragraph forms a twenty-second example.

The method may further comprise: Illuminating the one or more three-dimensional objects using the multifilament conductor to generate the light emitted from the one or more three-dimensional objects toward the optical diffuser. The features described in this paragraph in combination with the twenty-second example form a twenty-third example.

The method may further comprise illuminating the one or more three-dimensional objects using the multifilament conductor comprising: Transmitting light provided at a second end of the multifilament conductor to a first end of the multifilament conductor facing the optical diffuser; illuminating the one or more three-dimensional objects with at least a portion of the transmitted light. The features described in this paragraph in combination with the twenty-third example form a twenty-fourth example.

The method may include that generating the light emitted from the one or more three-dimensional objects toward the optical diffuser comprises: reflecting at least a portion of the light illuminating the one or more three-dimensional objects toward the optical diffuser, and/or luminescing the one or more three-dimensional objects in response to illuminating the one or more three-dimensional objects. The features described in this paragraph in combination with the twenty-third example or the twenty-fourth example form a twenty-fifth example.

The method may include that generating the image of the one or more three-dimensional objects based on pixels of the generated intensity pattern comprises: detecting the pixels of the generated intensity pattern provided by the multifilament conductor; generating the image of the one or more three-dimensional objects using the detected pixels of the generated intensity pattern using a trained neural network. The features described in this paragraph in combination with one or more of the twenty-second example through the twenty-fifth example form a twenty-sixth example.

A (non-transient, non-volatile, and/or non-transitory) storage medium may store program instructions that, when executed, cause the method of one or more of the twenty-second example through the twenty-sixth example to be performed. A computer program, computer program product, and/or computer readable medium may include instructions that, when executed by a processor, cause the processor to perform a method according to one or more of the twenty-second example through the twenty-sixth example.

The term "processor" may be understood as any type of entity that allows processing of data and/or signals. For example, the data and/or signals may be handled according to at least one (i.e., one or more than one) specific function performed by the processor. A processor may comprise or be formed from an analog circuit, a digital circuit, a mixed signal circuit, a logic circuit, a microprocessor, a central processing unit (CPU), a graphics processing unit (GPU), a digital signal processor (DSP), a programmable gate array (FPGA), an integrated circuit, or any combination thereof. Any other method of implementing the respective functions, described in more detail below, may also be understood to include a processor or logic circuit. It is understood that one or more of the method steps described in detail herein may be performed (e.g., implemented) by a processor, through one or more specific functions performed by the processor. The processor may therefore be configured to perform any of the information processing methods or components thereof described herein.

Flexible endoscopes can enable imaging in an opening, such as a natural or artificial body opening, by inserting them into the opening. Here, three-dimensional imaging may be required or desired. Further, for various openings, such as an examination of a brain via an artificial body opening (e.g., a comparatively small hole in the top of the skull), it may be necessary to ensure both electromagnetic compatibility of the flexible endoscope and a maximum diameter or width of less than 1 mm of the portion of the endoscope inserted into the opening. This can be achieved, for example, by using holographic endoscopes, which, however, have a very complex and thus cost-intensive optical setup. Therefore, it may also be necessary to achieve three-dimensional imaging with several (e.g., all) of the described requirements at a reduced cost. Various aspects relate to an optical system and a method by which three-dimensional imaging can be achieved with a simple optical setup. Further, the optical system and method may include a flexible section that may be inserted into an opening, which may have both a maximum diameter or width of less than 1 mm, if required or desired, and may provide electromagnetic compatibility.

FIG. 1A through FIG. 1D illustrate an optical system 100 according to various aspects. The optical system 100 may be, for example, an endoscope or an endoscope system.

The optical system 100 may include a multifilament conductor 102. The multifilament conductor 102 may be configured to transmit light waves. The multifilament conductor 102 may include a first end (e.g., a first free end) 104 and a second end (e.g., a second free end) 106. The multifilament conductor 102 may be configured to transmit light waves from the first end 104 to the second end 106, and vice versa. For example, the multifilament conductor 102 may comprise or consist of multiple fiber optic conductors (e.g., bundled together in a fiber optic cable). According to various aspects, the multifilament conductor 102 may comprise a plurality of optical fibers. Each optical fiber may be configured to transmit light waves. For example, the multifilament conductor 102 may have more than ten thousand (e.g., more than twenty thousand, e.g., more than forty thousand, e.g., more than one hundred thousand, e.g., more than two hundred thousand, etc.) optical fibers. According to various aspects, the multifilament conductor 102 may be bendable. Illustratively, the multifilament conductor 102 may be flexible, e.g., having a function-preserving bend radius of less than 50 cm. In this case, the optical system 100 may be, for example, a flexible endoscope or flexible endoscope system.

According to various aspects, the optical system 100 may include an optical diffuser 108. The optical diffuser 108 may be configured to project light irradiated onto the optical diffuser 108 as an intensity pattern onto the multifilament conductor 102, or to generate an intensity pattern based on the light irradiated onto the optical diffuser 108. For example, the first end 104 of the multifilament conductor 102 may face the optical diffuser 108 and the optical diffuser 108 may be configured to project light irradiated onto the optical diffuser 108 as an intensity pattern onto the first end 104 of the multifilament conductor 102. According to various aspects, the intensity pattern may represent phase information of the irradiated light. Illustratively, the optical diffuser 108 may encode phase information of the irradiated light into a two-dimensional intensity pattern. Illustratively, the optical diffuser 108 may encode phase information of the irradiated light into an intensity pattern, wherein the intensity pattern is formed due to diffuse scattering effects caused by the optical diffuser 108.

In physics, scattering is generally understood as the deflection of an object by interaction with another local object, more concretely the deflection of particle or wave radiation. The deflection of light can therefore be understood as a scattering of light.

Diffuse scattering can be, for example, diffuse transmission and/or diffuse reflection. A diffuse scattering (transmitting and/or reflecting), unlike a specular reflection or an image-transmitting transmission, can be understood as being irregularly dispersed, not sharply defined, and/or scattering without a uniform direction. Illustratively, in the case of transmitting scattering, the optical diffuser 108 may be translucent and non-image transmitting.

An optical diffuser (e.g., the optical diffuser 108) may be configured to diffusely reflect most (e.g., greater than 50%) of the reflected light and/or diffusely transmit most (e.g., greater than 50%) of the transmitted light. For example, the optical diffuser 108 may have a plurality of randomly distributed scattering centers and incident light may be scattered in transmission at the scattering centers.

An illustrative example of diffuse scattering in transmission is shown in FIG. 2A. A point (x, y, z) in space may emit a beam of light 210 in the direction of the optical diffuser 108. Illustratively, the point (x, y, z) may be a light point source 208. The light 210 emitted from the light point source 208 in the direction of the optical diffuser 108 may be diffusely scattered using the optical diffuser 108 (for example, diffusely transmitted as in the example illustrated in FIG. 2A). The diffuse scattering of the light 210 emitted from the light point source 208 may produce a plurality of light beams 212 that are emitted in the direction of the multifilament conductor 102. Imaging the plurality of light beams 212 in a common plane, such as on the first end 104 of the multifilament conductor 102, may produce an intensity pattern. The diffuse scattering of the incident light produced using the optical diffuser 108 may be described in terms of a point spread function. This point spread function depends on the position (x, y, z) of the light point source in space, so that each 3D position (x, y, z) of the light point source generates a unique intensity pattern. Examples of intensity patterns 402, 404, 406, 408, 410 (e.g., speckle patterns) generated based on a respective light point source are shown in FIG. 4A, where the light point source was vertically translated between each measured intensity pattern 402 to 410. Illustratively, the generated intensity patterns 402, 404, 406, 408, 410 show a shift as a function of the vertically translated light point source.

An intensity pattern generated by a light point source can be formed using an interference since a light point source is locally coherent. An intensity pattern generated by multiple light point sources may be formed by adding all intensity patterns of the multiple light point sources. Illustratively, for example, the intensity pattern (116, FIG. 1B) generated by the light 110 incident on the optical diffuser 108 may be a combination of the intensity patterns of all light point sources defining a respective surface of one or more three-dimensional objects 109 facing the optical diffuser 108. Illustratively, a 3D object may be or may be characterized by multiple light point sources. An example of a measured intensity pattern representing a 3D object is shown in FIG. 4B.

For example, the optical diffuser 108 may comprise a material that diffuses in transmission, such as matt glass (frosted glass) or a polymer. The polymer may be, for example, polytetrafluoroethylene or polytetrafluoroethylene-based (e.g., a Zenith Polymer®). According to various aspects, the optical diffuser 108 may include a diffuse scattering (e.g., diffuse reflective) coating. For example, the coating may comprise Al, Ag, Au, etc. According to various aspects, the optical diffuser 108 may be disposed at a distance (e.g., greater than 0.1 mm, e.g., greater than 0.2 mm, e.g., greater than 0.3 mm, etc.) from the first end 104 of the multifilament conductor 102. For example, a light transmissive material (e.g., glass) may be disposed between the optical diffuser 108 and the first end 104 of the multifilament conductor 102.

According to various aspects, the optical diffuser 108 may include a volume diffuser. For example, the optical diffuser 108 may comprise a short (e.g., having a length of less than 5 mm, e.g., having a length of less than 3 mm, e.g., having a length of less than 1 mm, e.g., having a length in a range of about 100 pm to about 5000 pm, e.g., having a length in a range of about 100 pm to 1 mm) multimode waveguide.

According to various aspects, the optical diffuser 108 may have a time-invariant point distribution function.

An intensity pattern can be understood such that different spatial regions of the pattern have different brightnesses from each other, or that differing intensities are present in different spatial regions of the pattern from each other. Intensities that are considered to be different front each other may have at least a 10% difference. Illustratively, the intensity pattern can be or be generated based on light-dark contrasts and/or based on color contrasts.

The multifilament conductor 102 may be configured to transmit the intensity pattern from the first end 104 to the second end 106. According to various aspects, the optical system 100 may include or be communicatively coupled to an evaluation system 112. The evaluation system 112 may be configured to receive the intensity pattern transmitted using the multifilament conductor 102. For example, the evaluation system 112 may include an optical fiber interface for this purpose. The evaluation system 112 may be configured to generate an image based on the intensity pattern transmitted via the multifilament conductor 102.

According to various aspects, light 110 irradiated onto the optical diffuser 108 may be emitted from the one or more three-dimensional objects 109. For example, the light 110 irradiated onto the optical diffuser 108 may be transmitted, reflected, and/or luminesced by the one or more three-dimensional objects 109. Illustratively, light may pass through the one or more three-dimensional objects 109 via transmission, may be reflected from the one or more three-dimensional objects 109 via reflection, and/or the one or more three-dimensional objects 109 may radiate the light via luminescence. At least a portion of this transmitted, reflected, and/or luminesced light may be irradiated (illustratively as the light 110) onto the optical diffuser 108. It is understood that the reflected, luminesced, and/or transmitted light from the one or more three-dimensional objects 109 toward the optical diffuser 108 is emitted from a portion of the one or more three-dimensional objects 109 facing the optical diffuser 108. For example, a surface of a 3D object may face the optical diffuser 108 and the surface may be described using a plurality of light point sources, wherein each light point source of the plurality of light point sources may reflect, luminesce, and/or emit transmitted light toward the optical diffuser 108.

Figure 1B:
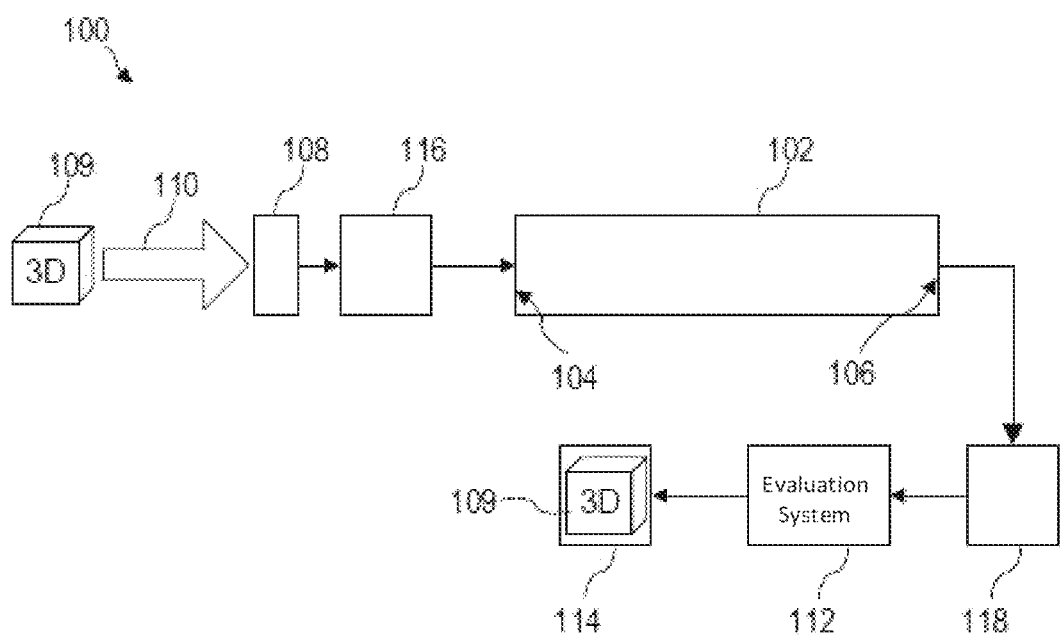
Figure 2C:
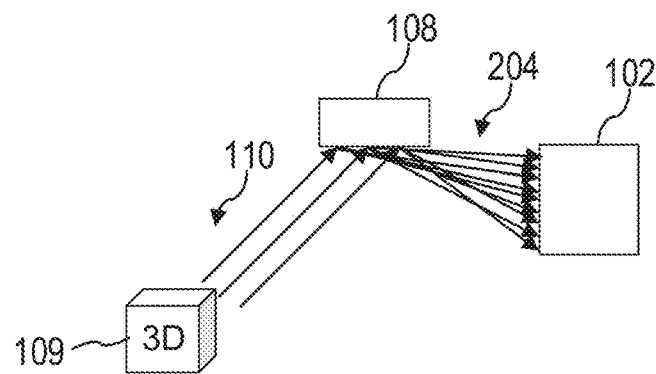

With reference to FIG. 1B, the optical diffuser 108 may be configured to project the light 110 irradiated onto the diffuser 108 as an intensity pattern 116 onto the multifilament conductor 102. The intensity pattern 116 may have or be, for example, a speckle pattern. As described above, the optical diffuser 108 may be configured to diffuse in transmission or reflection. Illustrative examples of this are shown in FIG. 2B and FIG. 2C. FIG. 2B illustratively shows a diffuse transmission of the light 110 irradiated onto the optical diffuser 108 using the optical diffuser 108. The optical diffuser 108 may be configured to project the scattered light rays 202 as the intensity pattern 116 onto the multifilament conductor 102. As described with reference to FIG. 2A, the intensity pattern 116 may be a combination of the intensity patterns generated by a plurality of light point sources of the one or more three-dimensional objects 109. FIG. 2C illustratively shows a diffuse reflection (e.g., a partial reflection, e.g., a total reflection) of the light 110 irradiated onto the optical diffuser 108 using the optical diffuser 108. The optical diffuser 108 may be configured to project the reflected light rays 204 as the intensity pattern 116 onto the multifilament conductor 102.

According to various aspects, the intensity pattern 116 may include phase information of the irradiated light 110 on the optical diffuser 108. According to various aspects, the phase information of the incident light 110 may characterize the light point sources of the incident light 110 (e.g., coordinates of respective light point sources). The phase information of the incident light 110 on the optical diffuser 108 may represent the one or more three-dimensional objects 109. Illustratively, the optical diffuser 108 may be configured to encode phase information of the irradiated light 110 having 3D information into a 2D intensity pattern. As a result, for example, no additional optics and/or additional electronics, such as a camera, are required at the first end 104 of the multifilament conductor 102 to convey 3D information. According to various aspects, the optical system 100 may not include a lens or electronics at the first end 104 of the multifilament conductor 102.

Figure 2D:
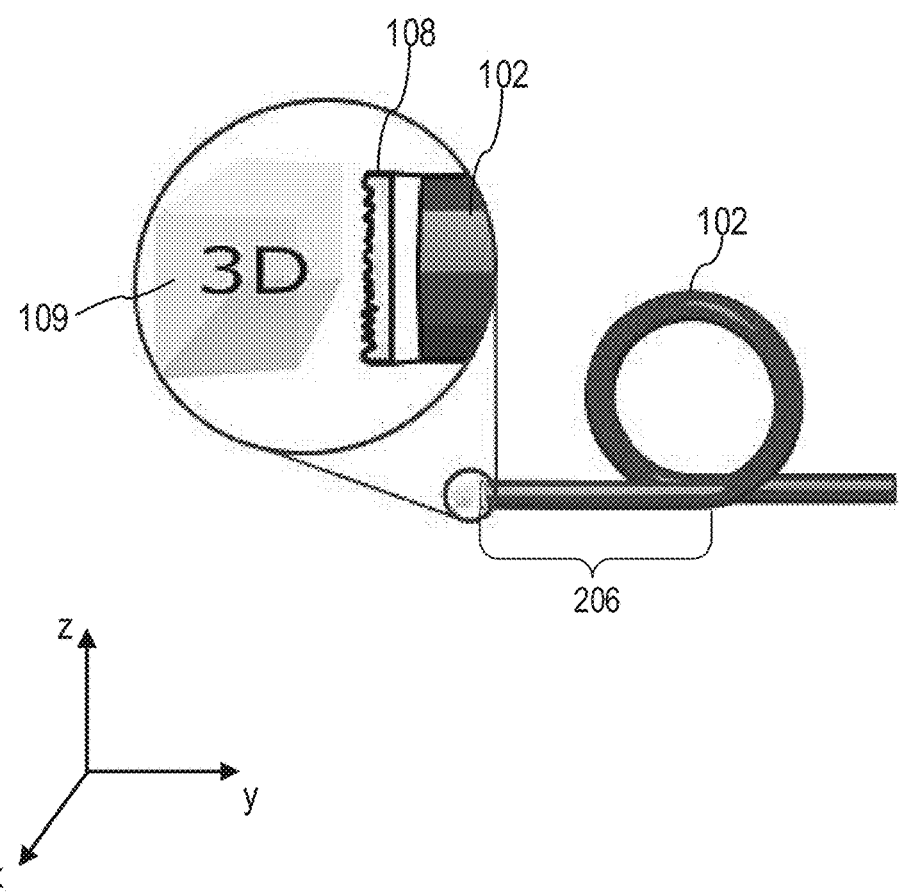

According to various aspects, the optical system 100 may be an endoscope or endoscopic system, and a portion 206 of the multifilament conductor 102 may be configured to be inserted into an opening (see, for example, FIG. 2D for an illustrative example). An opening, as used herein, may be, for example, a body opening of a living being (e.g., a human, e.g., an animal) or an opening of a device (e.g., an engineered device), apparatus, object, etc. The body opening may be a natural body opening (e.g., a mouth) or an artificial body opening (e.g., a cut in the skin or a hole in a bone or the like). The first end 104 of the multifilament conductor 102 facing the optical diffuser 108 may be a distal end of the endoscope, and the second end 106 of the multifilament conductor 102 may be a proximal end of the endoscope.

According to various aspects, the multifilament conductor 102 may be characterized by its conductor length and its conductor cross-section. In this regard, the conductor length may be a maximum length of the multifilament conductor 102 in a non-bent state. For example, the conductor cross-section of the multifilament conductor 102 (e.g., in the x-z plane in FIG. 2D) may have a cross-sectional area of one of the following shapes: a circle, a square, a rectangle, a triangle, a trapezoid, a parallelogram, an ellipse, a polygon, etc.

According to various aspects, the shape of the multifilament conductor 102 and the geometric dimensions defining the respective shape may be unchanged along the conductor length of the multifilament conductor 102. Illustratively, the conductor cross-section of the multifilament conductor 102 may be constant along the conductor length. Illustratively, the multifilament conductor 102 may be cylindrical in a straight line extended (not bent) state. For example, the conductor cross-section may have a circle as a cross-sectional area and the multifilament conductor 102 may form a circular cylinder in a straight line extended state. For example, the conductor cross-section may have a square as a cross-sectional area and the multifilament conductor 102 may form a cylinder with a square base (i.e., a cuboid) in a rectilinearly extended state. For example, the conductor cross-section may have a polygon as a cross-sectional area and the multifilament conductor 102 may form a prism in a rectilinearly extended state.

According to various aspects, the shape of the multifilament conductor 102 may be unchanged along the conductor length of the multifilament conductor 102, and the geometric dimensions defining the respective shape may change along the conductor length. Illustratively, the multifilament conductor 102 may have a geometric frustum in a straight line extended (non-bent) state. For example, the conductor cross-section may have a circle as the cross-sectional area and the multifilament conductor 102 may form a truncated cone in a straight line extended state. For example, the conductor cross-section may have a square as the cross-sectional area and the multifilament conductor 102 may form a truncated pyramid in a straight line extended state.

As previously described, the optical system 100 may be an endoscope or endoscope system, and the multifilament conductor 102 may include a portion 206 (e.g., a conductor section) configured to be inserted into an opening. According to various aspects, this portion 206 to be inserted may have a maximum conductor section dimension of less than 5 mm (e.g., less than 4 mm, e.g., less than 3 mm, e.g., less than 2 mm, e.g., less than 1 mm, e.g., less than 0.5 mm, etc.). For a circular conductor cross-section, the maximum dimension may be a maximum diameter of the conductor cross-section in the portion 206 of the multifilament conductor 102 to be inserted. For an angular (e.g., polygonal) conductor cross-section, the maximum extent may be a maximum width of the conductor cross-section in the portion 206 of the multifilament conductor 102 to be inserted. For example, the conductor cross-section may have a rectangular shape and the maximum width of the conductor cross-section may be the length of the diagonal of the rectangle. For example, the conductor cross-section may have a triangular shape and the maximum width of the conductor cross-section may be the maximum height (i.e., the height of the triangle having the largest value) of the triangle. It is noted that the optical diffuser 108 may also be inserted into the opening, and that the optical diffuser 108 may also have a maximum dimension less than or equal to the maximum dimension of the portion 206 of the multifilament conductor 102 to be inserted.

According to various aspects, the multifilament conductor 102 may have a first diameter (e.g., a first maximum diameter of the base) or a first width (e.g., a first maximum width of the base) at the first end 104. The optical diffuser 108 may have a second diameter (e.g., a second maximum diameter) or a second width (e.g., a second maximum width). According to various aspects, the second diameter or width may be equal to the first diameter or width. According to various aspects, a cross-sectional area of the optical diffuser 108 may have the same shape as the conductor cross-section of the multifilament conductor 102. For example, both the optical diffuser 108 and the multifilament conductor 102 may have a circular cross-section. An illustrative example of this is shown in FIG. 2D.

According to various aspects, the multifilament conductor 10:2 may include a plurality of optical fibers. For example, each optical fiber of the plurality of optical fibers may have substantially the same shape. For example, the cross-sectional area of an optical fiber may have a cross-sectional area of one of the following shapes: a circle, a square, a rectangle, a triangle, a trapezoid, a parallelogram, an ellipse, a polygon, etc.

Figure 3A:
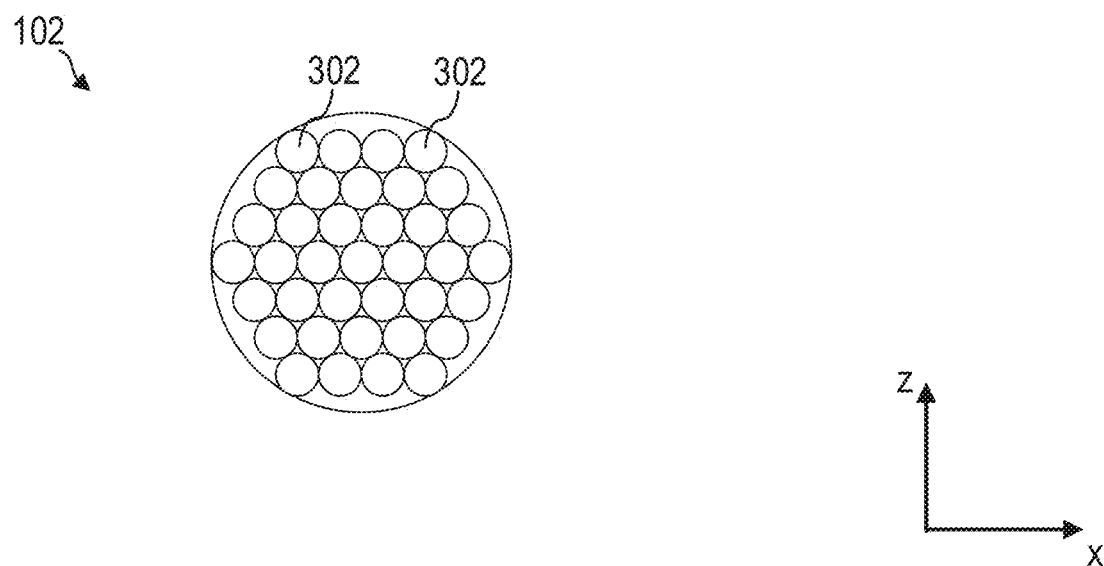
FIGS. 3A to 3D, respectively, a multifilament conductor according to various aspects.
Figure 3B:
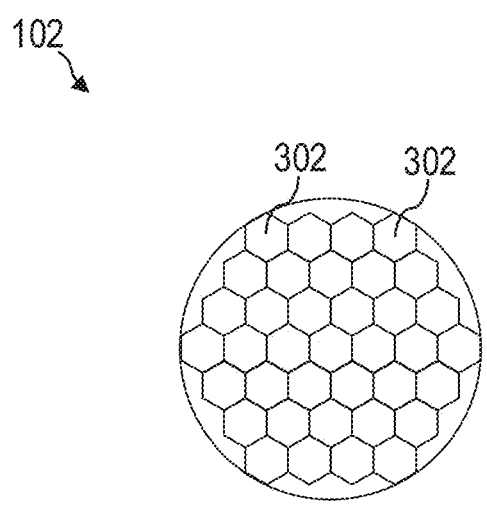

FIG. 3A and FIG. 3B each show an exemplary cross-section of a multifilament conductor 102 according to various aspects. The multifilament conductor 102 may include a plurality of optical fibers 302. Each optical fiber of the plurality of optical fibers 302 may physically contact adjacent optical fibers, at least in part. In this manner, the maximum extent of the conductor cross-section may be reduced. For example, the optical fibers of the plurality of optical fibers 302 may have a circular cross-section (FIG. 3A) or a polygonal cross-section (FIG. 3B). According to various aspects, the multifilament conductor 102 may comprise or be a coherent (e.g., ordered) multifiber bundle (a coherent plurality of optical fibers 302) or an incoherent (e.g., disordered) multifiber bundle (an incoherent plurality of optical fibers 302). According to various aspects, each optical fiber of the plurality of optical fibers 302 may be configured to transmit a single mode of light. Illustratively, each optical fiber of the plurality of optical fibers 302 may be a single mode optical fiber. As a result, complex calibration (e.g., in-situ calibration) may not be required compared to multimode optical waveguides, which involve mixing of light modes during transmission.

With reference to FIG. 19, the multifilament conductor 102 may be configured to transmit the intensity pattern 116 in the form of a plurality of pixels. According to various aspects, each optical fiber of the plurality of optical fibers 302 may transmit one pixel (e.g., exactly one pixel) of the plurality of pixels from the first end 104 of the multifilament conductor 102 to the second end 106 of the multifilament conductor 102. Transferring art image pixel using an optical fiber as used herein may be understood as transferring the light waves associated with the image pixel. For example, each pixel may represent a portion of the intensity pattern 116. Illustratively, the intensity pattern is thereby represented using the plurality of image pixels. Illustratively, each pixel of the plurality of pixels may be associated with an optical fiber of the plurality of optical fibers 302. For example, each pixel may be associated with exactly one optical fiber and vice versa. For example, the plurality of pixels and the plurality of optical fibers 302 may be objectively associated with each other. An exemplary intensity pattern 116 that is shown in FIG. 4B. FIG. 4C illustrates an illustrative mapping 400 of the exemplary intensity pattern 116 onto the multifilament conductor 102. According to various aspects, each optical fiber of the plurality of optical fibers 302 may represent a portion of the intensity pattern 116 that is mapped onto the optical fiber associated with the pixel. Illustratively, the optical fibers may define the pixels. The sum of the pixels transmitted via the plurality of optical fibers 302 may represent the intensity pattern 116. Illustratively, intensity pattern pixels 118 representing the intensity pattern 116 may be provided at the second end 106 of the multifilament conductor 102 (see FIG. 1B).

The evaluation system 112 may be configured to receive the plurality of pixels as intensity pattern pixels 118 (e.g., using the optical fiber interface). The evaluation system 112 may be configured to generate art image 114 based on the intensity pattern pixels 118. According to various aspects, the image 114 may represent the one or more three-dimensional objects 109. For example, the image 114 may represent one or more sides of the one or more three-dimensional objects 109 facing the optical diffuser 108. Illustratively, the image 114 may include depth information regarding the one or more three-dimensional objects 109.

Figure 1C:
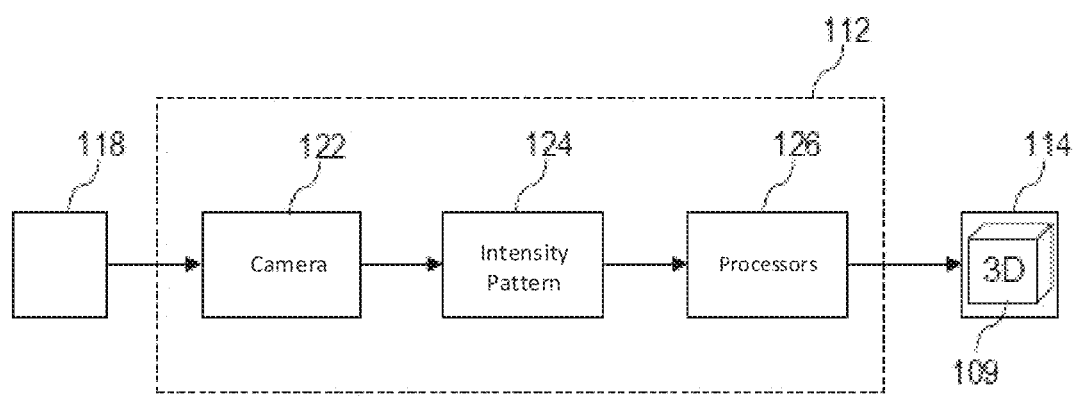

FIG. 1C illustrates the evaluation system 112 according to various aspects. The evaluation system 112 may include an imaging device, such as a camera 122 (e.g., a charge coupled device (CCD) camera). The imaging device is described below as an example of the camera 122. It is noted that any type of sensor that can detect light directly or indirectly may be used. The camera 122 may be configured to capture the intensity pattern image points 118 as an intensity pattern image 124. According to various aspects, the evaluation system 112 may include one or more processors 126. The one or more processors 126 may be configured to process the intensity pattern image 124 and generate the image 114. Illustratively, the image 114 representing the one or more three-dimensional objects 109 may be determined using a single shot.

The one or more processors 126 may include any type of logic implementing entity, as described above. The one or more processors 126 may implement logic using a memory device, for example, and/or may process data using the memory device.

According to various aspects, the one or more processors 126 may implement a trained neural network. For example, the one or more processors 126 may be configured to generate the image 114 from the intensity pattern image 124 using the trained neural network. Illustratively, the trained neural network may be configured to generate the image 114 in response to an input of the intensity pattern image 124 to the trained neural network. An exemplary training of a neural network set up for this purpose is described with reference to FIG. 9. Illustratively, the optical diffuser 108 can encode 3D information and the trained neural network can decode the 3D information. Illustratively, the optical diffuser 108 and the trained neural network form an encoder-decoder pair.

Figure 1D:
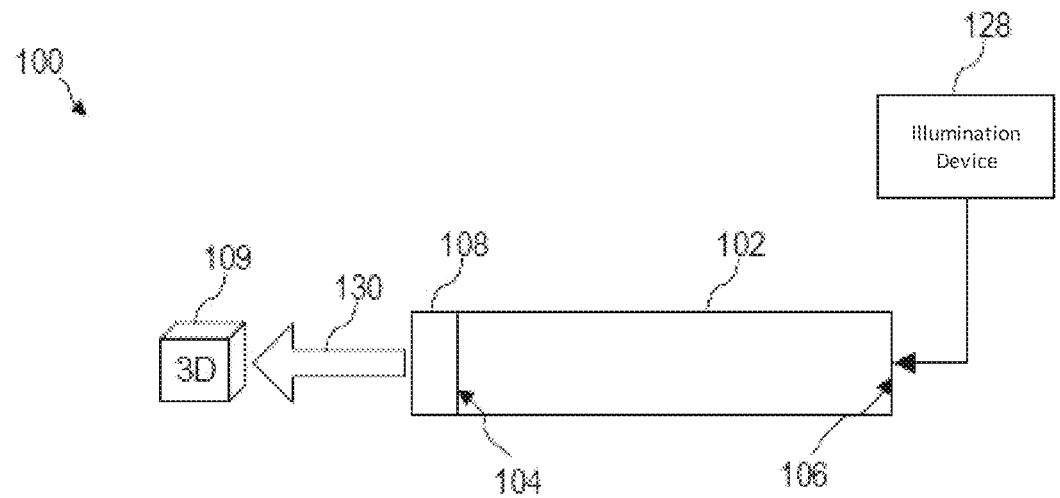
Figure 3C:
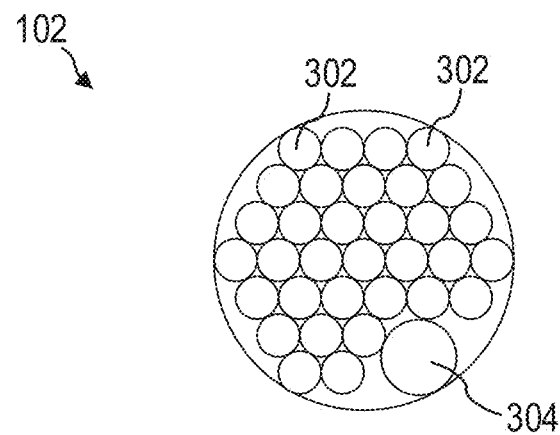
Figure 3D:
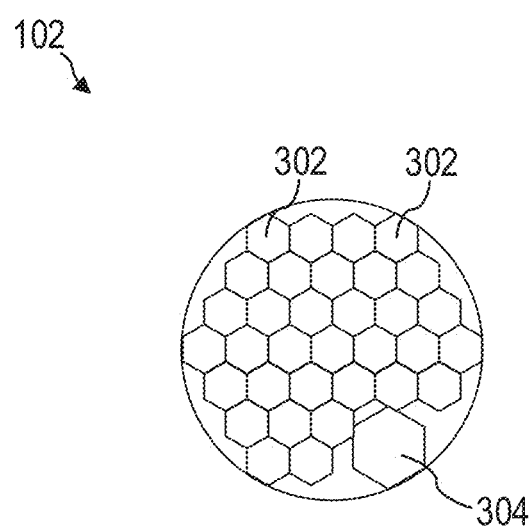

FIG. 1D illustrates the optical system 100 according to various aspects, wherein the optical system 100 may include or be communicatively coupled to an illumination device 128. The illumination device 128 may include a light source (e.g., a laser or laser light source). The illumination device 128 may be configured to generate light. The light source may be configured to generate light. The illumination device 128 may be configured to provide the generated light to the second end 106 of the multifilament conductor 102. The multifilament conductor 102 may be configured to transmit the light provided to the second end 106 of the multifilament conductor 102 by the illumination device 128 to the first end 104 of the multifilament conductor 102. According to various aspects, one or more optical fibers (e.g., all of the optical fibers) of the plurality of optical fibers 302 may be configured to transmit the light provided at the second end 106 of the multifilament conductor 102 by the illumination device 128 to the first end 104 of the multifilament conductor 102 (see FIG. 3A and FIG. 3B). According to various aspects, the multifilament conductor 102 may include one or more illumination waveguides 304 (see FIG. 3C and FIG. 3D). The one or more illumination waveguides 304 may be configured to transmit light provided at the second end 106 of the multifilament conductor 102 by the illumination device 128 to the first end 104 of the multifilament conductor 102. According to various aspects, the maximum cross-sectional dimension, such as the maximum diameter (FIG. 3C) or maximum width (FIG. 3D), of an illumination waveguide 304 may be different from the maximum cross-sectional dimension of an optical waveguide 302. For example, each illumination waveguide 304 of the one or more illumination waveguides 304 may have a larger maximum cross-sectional dimension than each optical waveguide of the plurality of optical waveguides 302.

According to various aspects, the illumination device 128 may be configured to provide polychromatic light (e.g., white light). Illustratively, the light provided at the second end 106 of the multifilament conductor 102 by the illumination device 128 may comprise or be polychromatic light.

According to various aspects, the illumination device 128 may be configured to produce light (e.g., light visible to the human eye) of various colors of light. The term "color of light," as used herein, may define a wavelength range of light within the electromagnetic spectrum. According to various aspects, illumination device 128 may be configured to generate and provide light of multiple mutually different colors of light to multifilament conductor 102 in temporal succession.

The light transmitted to the first end 104 of the multifilament conductor 102 may be emitted from the multifilament conductor 102 and may at least partially illuminate the one or more three-dimensional objects 109. Illustratively, the one or more three-dimensional objects 109 may be illuminated by the multifilament conductor 102 using the illumination device 128. It is understood that, in this regard, a portion facing the optical diffuser 108 (e.g., a facing surface of the facing portion) of the one or more three-dimensional objects 109 may be illuminated.

According to various aspects, the multifilament conductor 102 may be configured to only partially illuminate the one or more three-dimensional objects 109 using one or more optical fibers of the plurality of optical fibers 302. For example, the portion of the one or more three-dimensional objects 109 facing the optical diffuser 108 may be or may be divided into a first portion and a second portion different from the first portion, and the optical system 100 may be configured to illuminate only the first portion or only the second portion.

An illumination of the one or more three-dimensional objects 109 may be understood herein as a direct illumination using the optical diffuser 108. In contrast, light that is incident on the one or more three-dimensional objects 109 but is reflected from at least one other object between the optical diffuser 108 and the one or more three-dimensional objects 109 may be understood herein as indirect illumination.

According to various aspects, the optical system 100 may achieve maximum illumination by transmitting and emitting light provided by the illumination device 128 using all of the optical fibers of the plurality of optical fibers 302. According to various aspects, the optical system 100 may achieve only partial illumination by transmitting and emitting light provided by the illumination device 128 using selected optical fibers of the plurality of optical fibers 302 (e.g., less than all optical fibers of the plurality of optical fibers 302).

Figure 5:
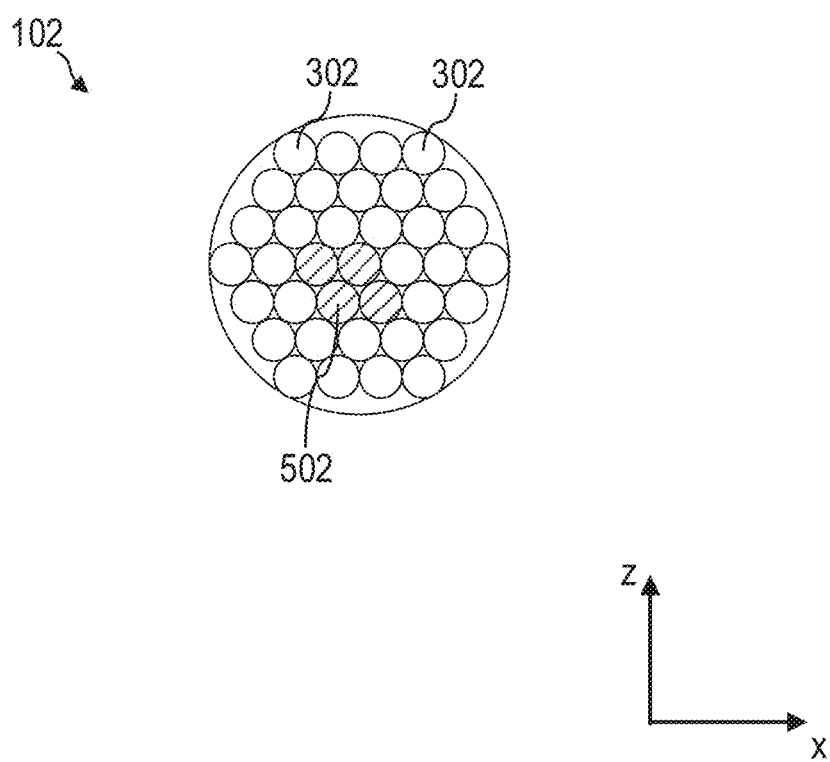
FIG. 5 an illustration of the principle of structural lighting, according to various aspects.

The illumination device 128 may be configured to selectively provide the light to one or more optical fibers of the plurality of optical fibers 302. For example, each optical fiber of the plurality of optical fibers 302 may be configured to transmit the light provided at the second end 106 of the multifilament conductor 102, and the illumination device 128 may be configured to selectively provide the light to one or more optical fibers of the plurality of optical fibers 302. An illustrative example of this is shown in FIG. 5. For example, the illumination device 128 may provide light to selected optical fibers 502 of the plurality of optical fibers 302. For example, the optical system 100 may include an opening and the opening may be configured to provide light generated by the illumination device 128 to selected optical fibers 502 of the plurality of optical fibers 302. For example, the illumination device 128 may be configured to generate a focused beam of light and may be configured to provide the focused beam of light to selected optical fibers 502 of the plurality of optical fibers 302. For example, the illumination device 128 may be configured to selectively irradiate light into the selected optical fibers 502 of the plurality of optical fibers 302. Illustratively, the one or more three-dimensional objects 109 may be selectively illuminated only partially in this manner. For example, the illuminated region of the one or more three-dimensional objects 109 may be the portion of the surface of the one or more three-dimensional objects 109 that has more than 70% (e.g., more than 80%, e.g., more than 90%, e.g., more than 95%) of the light intensity irradiated onto the one or more three-dimensional objects 109.

According to various aspects, the illumination device 128 may be configured to sequentially provide light to at least partially different optical fibers of the plurality of optical fibers 302. Illustratively, different parts (e.g., regions, e.g., sections) of the one or more three-dimensional objects 109 may be selectively, sequentially illuminated in this manner. For example, portions of the one or more three-dimensional objects 109 that are illuminated differently from one another may have an illuminated area that is different by at least 30% (e.g., at least 40%, e.g., at least 50%, etc.). For example, using selected first optical waveguides of the plurality of optical waveguides 302, a first region of the one or more three-dimensional objects 109 may be illuminated with more than 70% of the light intensity irradiated to the one or more three-dimensional objects 109, and temporally thereafter, using selected second optical waveguides, which comprise at least one optical waveguide of the plurality of optical waveguides 302 that is different from the first optical waveguides, a second region of the one or more three-dimensional objects 109 can be illuminated with more than 70% of the light intensity irradiated onto the one or more three-dimensional objects 109, wherein the illuminated first region and the illuminated second region are different from each other by at least 30%. Illustratively, the one or more three-dimensional objects 109 can thereby be illuminated in a structured manner.

According to various aspects, light emitted toward the one or more three-dimensional objects 109 from the multifilament conductor 102 may be reflected from the one or more three-dimensional objects 109, and at least a portion of the reflected light may be irradiated on the optical diffuser 108 as light 110, as described with reference to FIG. 1A and FIG. 1B.

According to various aspects, light emitted toward the one or more three-dimensional objects 109 from the multifilament conductor 102 may excite the one or more three-dimensional objects 109 to luminesce, and at least a portion of the luminesced light may be irradiated on the optical diffuser 108 as light 110, as described with reference to FIG. 1A and FIG. 1B.

According to various aspects, the evaluation system 112 may be configured to detect multiple mutually different colors of light. For example, the camera 122 may be configured to detect multiple light colors that are different from each other (see FIG. 1C). For example, the evaluation system 112 may be configured to detect multiple wavelength ranges that are at least partially different from each other. For example, the camera 122 may have or be a multispectral camera. Illustratively, the evaluation system 112 may capture multiple color channels.

According to various aspects, the illumination device 128 may be configured to generate polychromatic light and at least a portion of the polychromatic light may be reflected off the one or more three-dimensional objects 109 toward the optical diffuser 108. It is understood that different modes of a monochromatic laser are not understood to be polychromatic light. The optical diffuser 108 may be configured to project the reflected polychromatic light as an intensity pattern 116 onto the first end 104 of the multifilament conductor 102. The evaluation system 112 may be configured to detect a plurality of different light colors of the intensity pattern 116 comprising information of the diffusely scattered (e.g., diffusely reflected, e.g., diffusely transmitted) polychromatic light as a respective intensity pattern image 124. The evaluation system 112 may be configured to generate the image 114 based on all of the acquired intensity pattern images 124. For example, the one or more processors 126 may implement the trained neural network, which may be configured to output the image 114 in response to an input of all detected intensity pattern images 124. As an illustrative example, the polychromatic light may have or be white light, for example, and the evaluation system 112 may be configured to, for example, acquire a respective intensity pattern image for blue light, green light, and red light, and generate the image representing the one or more three-dimensional objects 109 using the intensity pattern image acquired for the blue light, the intensity pattern image acquired for the green light, and the intensity pattern image acquired for the red light. Illustratively, the information content of the light can be increased in such a manner that, for example, a resolution of the image representing the one or more three-dimensional objects 109 can be improved.

According to various aspects, the illumination device 128 may be configured to generate light of a plurality of different light colors in temporal succession, and for each light color, at least a portion of the light may be reflected off the one or more three-dimensional objects 109 toward the optical diffuser 108. The optical diffuser 108 may be configured to project the reflected light of the respective light color as an intensity pattern 116 onto the first end 104 of the multifilament conductor 102. The evaluation system 112 may be configured to detect the light having the light colors generated by the illumination device 128 as a respective intensity pattern image 124. The evaluation system 112 may be configured to generate the image 114 based on the intensity pattern images 124 captured for all colors of light. For example, the one or more processors 126 may implement the trained neural network, which may be configured to output the image 114 in response to an input of all of the intensity pattern images 124 captured for the different light colors. As an illustrative example, the illumination device 128 may be configured to first generate blue light, and the evaluation system 112 may be configured to acquire an intensity pattern image for the blue light; temporally thereafter, the illumination device 128 may generate red light, and the evaluation system 112 may be configured to acquire an intensity pattern image for the red light and generate the image representing the one or more three-dimensional objects 109 using the intensity pattern image acquired for the blue light and the intensity pattern image acquired for the red light. Illustratively, a resolution of the image representing the one or more three-dimensional objects 109 can be improved in this manner.

As described herein, the optical system 100 may be configured to illuminate the one or more three-dimensional objects 109 in a structured manner. According to various aspects, only a portion of the one or more three-dimensional objects 109 may be selectively illuminated in this regard. According to various aspects, the optical system 100 may be configured to successively illuminate at least partially different portions of the one or more three-dimensional objects 109. In this regard, the evaluation system 112 may be configured to capture a respective intensity pattern image 124 for each illuminated portion of the one or more three-dimensional objects 109. According to various aspects, the evaluation system 112 may be configured to generate the image 114 representing the one or more three-dimensional objects 109 using all of the acquired intensity pattern images 124. For example, the one or more processors 126 may implement the trained neural network, which may be configured to output the image 114 in response to an input of all of the intensity pattern images 124 acquired for the various portions of the one or more three-dimensional objects 109. Illustratively, a portion of each of the one or more three-dimensional objects 109 may be sequentially captured in this manner, which may be assembled into the image 114 representing the one or more three-dimensional objects 109. This may, for example, improve a resolution of the generated image. Illustratively, the complexity of captured intensity pattern images may be reduced in this manner, which may, for example, improve a reconstruction of the image.

According to various aspects, the optical system 100 may be configured to illuminate the one or more three-dimensional objects 109 in a structured manner using polychromatic light, and the evaluation system 112 may be configured to detect a plurality of light colors of the polychromatic light for each structurally illuminated portion of the one or more three-dimensional objects 109 and to generate an associated intensity pattern image 124. According to various aspects, the optical system 100 may be configured to illuminate the one or more three-dimensional objects 109 in a structured manner with light of a plurality of mutually different light colors in a temporally successive manner. Illustratively, a portion of each of the one or more three-dimensional objects 109 may be illuminated in temporal succession with a plurality of mutually different light colors. The evaluation system 112 may be configured to capture a respective intensity pattern image 124 for each structurally illuminated portion of the one or more three-dimensional objects 109, for each light color of the plurality of mutually different light colors. According to various aspects, the evaluation system 112 may be configured to generate the image 114 using all (for each portion of the one or more three-dimensional objects 109 and for each light color respectively detected for each portion) of the generated intensity pattern images 124. For example, the one or more processors 126 may implement the trained neural network, which may be configured to output the image 114 in response to an input of all intensity pattern images 124 captured for the various light colors for all portions of the one or more three-dimensional objects 109. Illustratively, multiple portions of the one or more three-dimensional objects 109 and/or multiple colors of light may be evaluated together in this manner. For example, an image 114 generated in this manner may have significantly increased resolution.

The optical system 100 described herein may be, for example, a flexible endoscope or flexible endoscope system. Various endoscopes, such as video endoscopes and capsule endoscopes, may include cameras at a distal end of the endoscope that may be inserted into an opening of an object (e.g., a body opening), which may affect electromagnetic compatibility, for example, in endoscopy of living beings. Moreover, this requires a comparatively large cross-sectional dimension (e.g., more than 10 mm) of the portion of the endoscope to be inserted, so that small openings, such as a small opening in the skull for examining the brain, cannot be examined. Various endoscopes may have lens systems (e.g., objective and lens) at the distal end of the endoscope, which also results in a comparatively large cross-sectional expansion of the portion of the endoscope to be inserted. A reduction of the cross-sectional expansion can be achieved, for example, using multimode multifilament conductors, which, however, require an in-situ calibration of the transmission properties (which may depend, for example, on a bending of the optical fibers, a wavelength, a temperature, etc.) and a precoding of the light irradiated at the proximal end of the endoscope. However, this in-situ calibration requires access to both the proximal end and the distal end of the endoscope, so in-situ calibration (e.g., after the endoscope has been inserted into a brain) may be limited or even impossible. According to various aspects, the optical system 100 described herein may be an endoscope that addresses the above issues such that an endoscope with a reduced cross-sectional dimension may be provided. Further, the optical system 100 described herein enables 3D imaging.

FIG. 6 illustrates a flowchart 600 of a method (e.g., imaging method) according to various aspects. The method may include generating light emitted from one or more three-dimensional objects toward an optical diffuser (in 602).

The method may comprise generating, using the optical diffuser (in 604), an intensity pattern as an image of the light emitted toward the optical diffuser. According to various aspects, the intensity pattern may represent phase information of the light.

The method may comprise generating an image of the one or more three-dimensional objects based on pixels of the generated intensity pattern, wherein the pixels of the generated intensity pattern are supplied using a multifilament conductor (in 606).

FIG. 7 shows a flowchart 700 of a method (e.g., imaging method) according to various aspects. FIGS. 8A through 8E illustrate a schematic flowchart of the method exemplary of optical system 100.

Figure 8A:
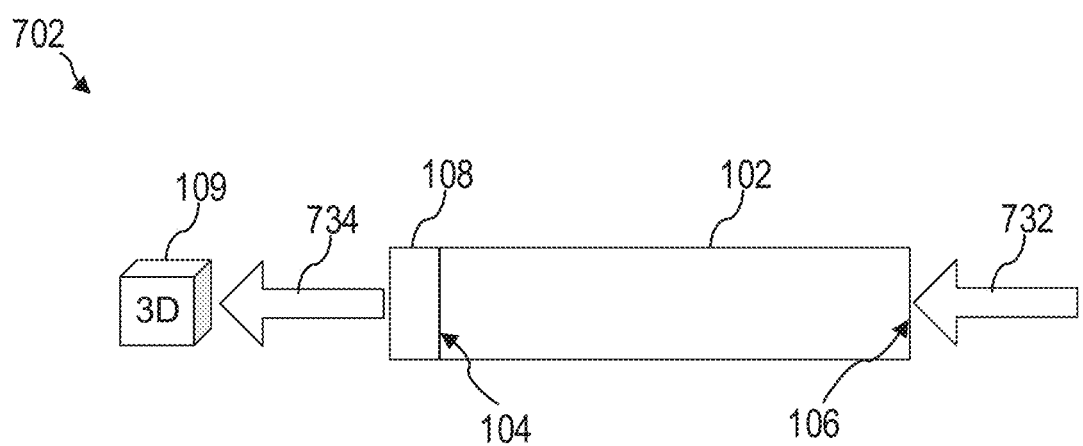
FIGS. 8A to 8E a schematic flow of an imaging method using an optical system, according to various aspects.

The method may comprise illuminating the one or more three-dimensional objects 109 using the multifilament conductor 102 (shown in 702, FIG. 8A). According to various aspects, the method may comprise transmitting light 732 provided at the second end 106 of the multifilament conductor 102 to the first end 104 of the multifilament conductor 102 facing the optical diffuser 108. According to various aspects, the method may comprise illuminating the one or more three-dimensional objects 109 with at least a portion of the transmitted light 734.

Figure 8B:
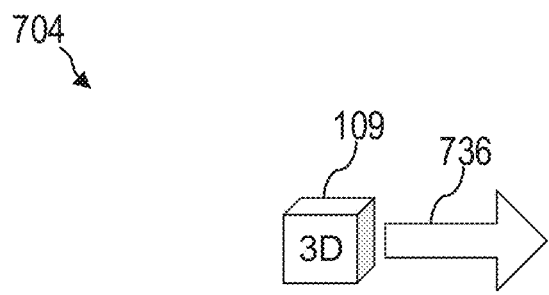

The method may include generating light 736 emitted from the one or more three-dimensional objects toward the optical diffuser (shown in 704, FIG. 8B). According to various aspects, at least a portion of the transmitted light 734 used to illuminate the one or more three-dimensional objects 109 may be reflected toward the optical diffuser 108. According to various aspects, the one or more three-dimensional objects 109 may luminesce in response to illuminating the one or more three-dimensional objects 109.

Figure 8C:
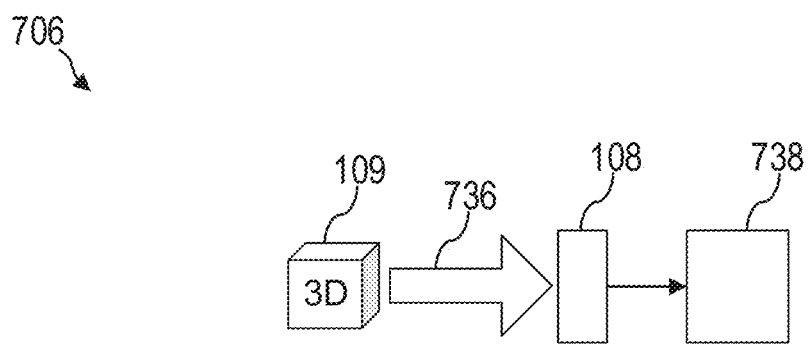

The method may include generating, using the optical diffuser, an intensity pattern 738 as a mapping of light 736 generated by the one or more three-dimensional objects 109 and emitted toward the optical diffuser (shown in 706, FIG. 8C). According to various aspects, the intensity pattern may represent phase information of the light.

Figure 8D:
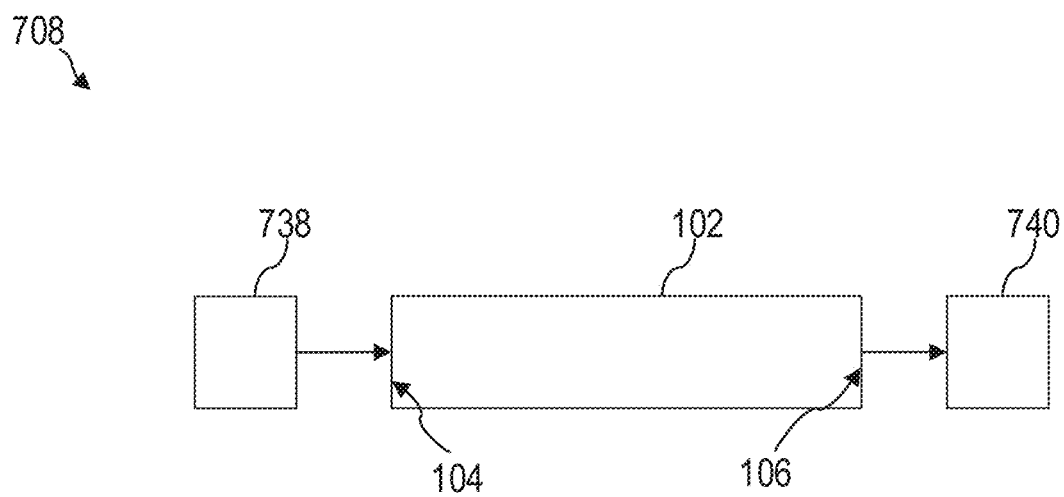

The method may comprise transferring the intensity pattern 738 in the form of a plurality of intensity pattern pixels 740 from the first end 104 of the multifilament conductor 102 to the second end 106 of the multifilament conductor 102 (at 708, FIG. 8D).

Figure 8E:
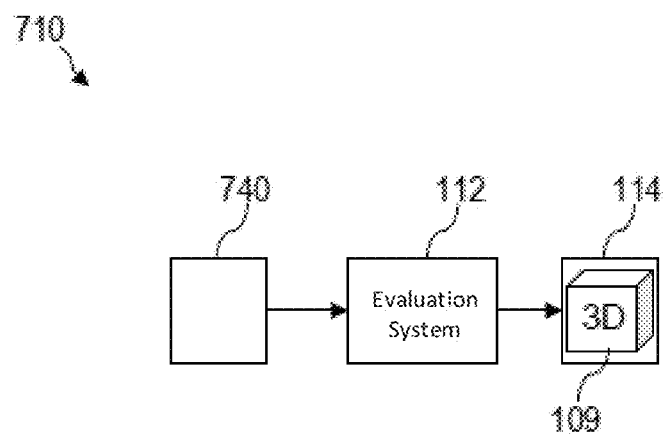

The method may comprise generating an image 114 of the one or more three-dimensional objects 109 based on the intensity pattern pixels 740 (at 710, FIG. 8E).

Figure 9:
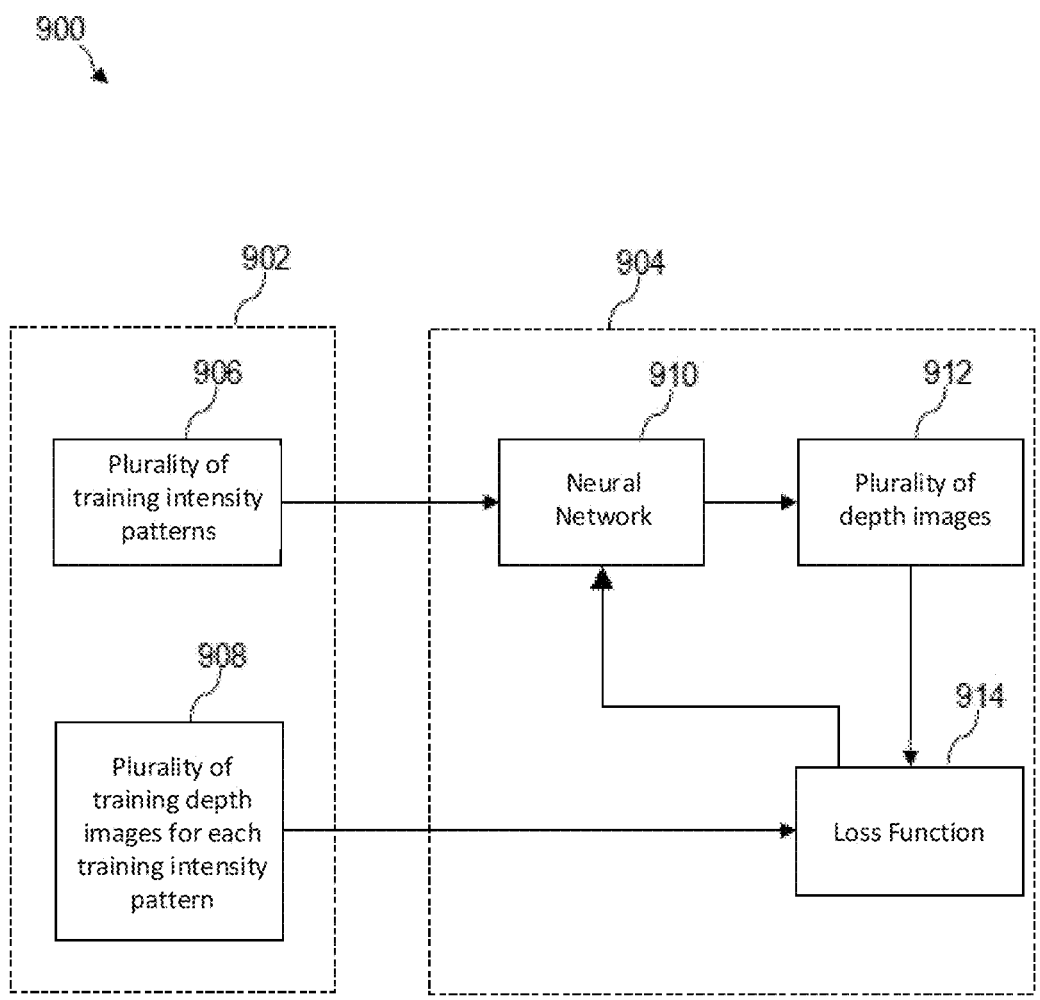
FIG. 9 a training device according to various aspects.

FIG. 9 shows a training device 900 for training a neural network 910 according to various aspects.

A neural network can be any type of neural network, such as an autoencoder network, a convolutional neural network (CNN), a variational autoencoder network (VAE), a sparse autoencoder network (SAE), a recurrent neuroanal network (RNN), a deconvolutional neural network (DNN), a generative adversarial network (GAN), a forward-thinking neural network, a sum-product neural network, etc.), have or be. The neural network can have any number of layers.

The training device 900 may include a memory device 902 and one or more processors 904. The memory device 902 may include at least one memory. The memory may be used, for example, in processing performed by a processor. A memory used in the aspects may be a volatile memory, for example, a DRAM (dynamic random access memory), or a non-volatile memory, for example, a PROM (programmable read-only memory), an EPROM (erasable PROM), an EEPROM (electrically erasable PROM), or a flash memory, such as a floating gate memory device, a charge trapping memory device, an MRAM (magnetoresistive random access memory), or a PCRAM (phase change random access memory). The memory device 902 may be configured to store code (e.g., program code), for example, to implement a neural network.

The storage device 902 may be configured to store a plurality of training intensity patterns 906. Each training intensity pattern of the plurality of training intensity patterns 906 may be a speckle pattern, for example. The storage device 902 may be configured to store, for each training intensity pattern of the plurality of training intensity patterns 906, an associated plurality of training depth images 908. Each training depth image of the plurality of training depth images 908 may be associated with a respective distance to an optical diffuser (e.g., the optical diffuser 108). Illustratively, the training depth images may define a predefined volume.

According to various aspects, an optical system, such as optical system 100, may be used to detect a respective intensity pattern for each light point source of a plurality of light point sources within the predefined volume. For example, an object represented in a training depth image may be viewed as a plurality of light point sources. According to various aspects, a training intensity pattern of the plurality of training intensity patterns 906 may be generated by superimposing the intensity patterns associated with the light point sources of all objects represented in the training depth images associated with the training intensity pattern into the training intensity pattern.

The one or more processors 904 may be configured to implement the neural network 910. The neural network 910 may be configured to generate a plurality of depth images 912 in response to an input of a training intensity pattern. For example, the neural network 910 may include a plurality of subnetworks and each subnetwork may be configured to generate a depth image of the plurality of depth images 912. For example, a subnetwork of the neural network 910 may be a U-Net. Each depth image of the plurality of depth images 912 may be associated with a training depth image of the plurality of training depth images 908. The training depth image associated with a depth image may represent the same distance from the optical diffuser as the training depth image.

According to various aspects, the one or more processors 904 may be configured to determine, using a loss function 914, at least one loss value between the generated depth image and the associated training depth image. For example, the one or more processors 904 may be configured to determine, using the loss function 914, a loss value between the generated depth image and the associated training depth image for each pixel of the generated depth image. According to various aspects, the one or more processors 904 may be configured to train the neural network 910 by adjusting the neural network 910 such that the at least one loss value of each depth image of the plurality of depth images 912 is reduced (e.g., minimized) According to various aspects, the neural network 910 may generate a respective associated plurality of training information images 912 for each training intensity pattern of the plurality of training intensity patterns 906, and the one or more processors 904 may be configured to determine at least one loss value between the generated depth image and the associated training depth image for each training information image and adapt the neural network 910 such that the loss values are reduced (e.g., minimized). The neural network 910 may be adapted, for example, by backpropagating (e.g., using a backpropagation algorithm) the determined loss values.

In an illustrative example, 32×32×9 (width×height× depth) light point sources within a volume of 100×100×400 pm$^3$ may be detected by the optical system 100 as a respective intensity pattern. Further, for each of the nine depths, a respective 32×32 pixel image may be generated, where each pixel may have either a value equal to "0" or a value equal to "1". Illustratively, each pixel of the 32×32 pixels can thus be associated with a light point source of the 32×32 light point sources (e.g., bijective). For all of the nine depths, the intensity pattern of each light point source whose associated pixel has the value "1" can be superimposed to form a common intensity pattern. Illustratively, the common intensity pattern may be a superposition of the intensity patterns of all light point sources across all depths. According to various aspects, the common intensity pattern may be a training intensity pattern of the plurality of training intensity patterns 906. According to various aspects, the plurality of training intensity patterns 906 may be generated in this manner.

Illustratively, the neural network 910 may be trained such that the trained neural network outputs a plurality of images representing depth of objects in response to an input of an intensity pattern. FIG. 10 illustrates exemplary depth images 1002A, 1004A, 1006A that a trained neural network may output in accordance with various aspects for the exemplary intensity pattern 116 illustrated in FIG. 4B, and respective associated training depth images 1002B, 1004B, 1006B. For example, a first depth image 1002. A may be associated with a first distance to the optical diffuser 108, and a first training depth image 1002B may be associated with the first depth image 1002A. For example, a second depth image 1004A may be associated with a second distance to the optical diffuser 108 different from the first distance, and the second depth image 1004A may be associated with a second training depth image 1004B. For example, a third depth image 1006A may be associated with a third distance to the optical diffuser 108 different from the first distance and the second distance, and the third depth image 1006A may be associated with a third training depth image 1006B. Illustratively, the trained neural network may predict the depth images 1002A, 1004A, 1006A and the training depth images 1002B, 1004B, 1006B may have or be the ground truth data of the depth images 1002A, 1004A, 1006A.

According to various aspects, the neural network 910 may be trained such that, in response to an input of an intensity pattern, the trained neural network outputs an image representing the one or more objects in three dimensions (comprising depth information). Illustratively, in response to an input of an intensity pattern comprising 3D information of one or more objects in an encoded manner, the trained neural network may generate an image representing the one or more objects in three dimensions.

As described herein, the evaluation system 112 may be configured to detect a plurality of mutually different light colors. According to various aspects, the neural network 910 may be trained such that the trained neural network outputs an image comprising depth information (e.g., representing objects in three dimensions) in response to an input of a plurality of detected intensity patterns each associated with a light color of the plurality of mutually different light colors. In this regard, the plurality of training intensity patterns 906 may comprise a plurality of groups of training intensity patterns, wherein each group comprises a plurality of training intensity patterns, and wherein the each training intensity pattern of a group of training intensity patterns is associated with a respective light color of a plurality of light colors. According to various aspects, each group of depth intensity patterns of the plurality of training intensity patterns 906 may have associated therewith a respective plurality of training depth images 908. Illustratively, each group of training intensity patterns may include, for example, a training intensity pattern of blue light, a training intensity pattern of red light, and a training intensity pattern of green light, and each group may have associated therewith the respective plurality of training depth images 908. According to various aspects, a respective intensity pattern in each light color of the plurality of light colors may be detected by an optical system, such as optical system 100, for each light point source of a plurality of light point sources within the predefined volume. According to various aspects, a training intensity pattern of each light color of the plurality of light colors may be generated by superimposing the intensity patterns of the respective light color associated with the light point sources of all objects represented in the training depth images associated with the training intensity pattern of the respective light color to the training intensity pattern of the respective light color. The neural network 910 may be configured to generate a plurality of depth images 912 in response to an input of each training intensity pattern of a respective group of training intensity patterns. Each depth image of the plurality of depth images 912 may be associated with a training depth image of the plurality of training depth images 908. The training depth image associated with a depth image may represent the same distance from the optical diffuser as the training depth image. According to various aspects, the one or more processors 904 may be configured to determine at least one loss value between the generated depth image and the associated training depth image using the loss function 914 and to train the neural network 910 by adjusting the neural network 910 such that the at least one loss value of each depth image of the plurality of depth images 912 is reduced (e.g., minimized).

The invention claimed is:

1. An optical system comprising:
a multifilament conductor,
an optical diffuser configured to project an intensity pattern onto the multifilament conductor,
the intensity pattern representing phase information of light emitted front one or more three-dimensional objects;
wherein the multifilament conductor is configured to transmit the intensity pattern in the form of a plurality of pixels to an evaluation system, and
wherein the evaluation system is configured to generate art image based on the intensity pattern transmitted by the multifilament conductor, the image representing the one or more three-dimensional objects.

2. The optical system according to claim 1, wherein the optical diffuser is configured to diffuse in transmission and/or in reflection.

3. The optical system according to claim 1,
wherein the multifilament conductor has a first diameter or width at a first end facing the optical diffuser, and
wherein the optical diffuser has a second diameter or width substantially equal to the first diameter or width.

4. The optical system according to claim 1, wherein the multifilament conductor is configured to only partially illuminate the one or more three-dimensional objects using one or more optical fibers of the multifilament conductor.

5. The optical system according to claim 1, wherein the multifilament conductor is configured to illuminate the one or more three-dimensional objects using light provided to the multifilament conductor by an illumination device.

6. The optical system according to claim 5, wherein the light provided to the multifilament conductor via the illumination device comprises polychromatic light.

7. The optical system according to claim 5, wherein the illumination device is further configured to provide light to the multifilament conductor.

8. The optical system according to claim 7, wherein the illumination device is configured to provide polychromatic light to the multifilament conductor; and
wherein the evaluation system is configured to detect a plurality of light colors of the intensity pattern transmitted by the multifilament conductor and to generate the image based on the detected plurality of light colors of the intensity pattern.

9. The optical system according to claim 7, wherein the illumination device is configured to provide temporally successive visible light of a plurality of mutually different light colors to the multifilament conductor;
wherein the multifilament conductor is configured to transmit, for each light color of the plurality of mutually different light colors, a respective intensity pattern representing phase information of light emitted from the one or more three-dimensional objects in the form of a plurality of pixels to the evaluation system; and
wherein the evaluation system is configured to generate the image based on the intensity patterns transmitted by the multifilament conductor for the plurality of mutually different colors of light.

10. The optical system according to claim 7, wherein the illumination device is configured to selectively provide light to one or more optical fibers of the multifilament conductor.

11. The optical system according to claim 1, wherein a portion of the multifilament conductor is configured for insertion into an opening, wherein the portion of the multifilament conductor and the optical diffuser each have a diameter and/or a width of less than 1 mm.

12. The optical system according to claim 1, wherein the evaluation system is configured to generate the image based on the intensity pattern transmitted via the multifilament conductor using a trained neural network.

13. The optical system according to claim 1, wherein the optical system is an endoscope or an endoscope system.

14. The optical system of claim 1, wherein the optical diffusor projecting the intensity pattern onto the multifilament conductor comprises the optical diffusor projecting a two-dimensional intensity pattern onto the multifilament conductor;
wherein the phase information is three-dimensional, and wherein the optical diffusor is further configured to encode the three-dimensional phase information as the two-dimensional intensity pattern.

15. The optical system of claim 14, wherein the image is a three-dimensional image, and wherein the evaluation system is further configured to generate the three-dimensional image based on the two-dimensional intensity pattern in which the phase information is encoded.

16. The optical system of claim 12, wherein the neural network is configured to output a plurality of images representing depth of objects in response to an input of an intensity pattern.

17. A method comprising:
generating light emitted from one or more three-dimensional objects toward an optical diffuser;
generating an intensity pattern as a depiction of the light emitted toward the optical diffuser, the intensity pattern representing phase information of the light; and
generating an image of the one or more three-dimensional objects based on pixels of the generated intensity pattern, wherein the pixels of the generated intensity pattern are provided by a multifilament conductor.

18. The method according to claim 17, further comprising:
Illuminating the one or more three-dimensional objects using the multifilament conductor to generate the light emitted from the one or more three-dimensional objects toward the optical diffuser.

* * * * *